US007049475B2

(12) United States Patent
Inagaki

(10) Patent No.: US 7,049,475 B2
(45) Date of Patent: May 23, 2006

(54) ORGANIC COMPOUND DECOMPOSING METHOD

(75) Inventor: Yasuhito Inagaki, Kanagawa (JP)

(73) Assignee: Sony Corporation (JP)

(*) Notice: Subject to any disclaimer, the term of this patent is extended or adjusted under 35 U.S.C. 154(b) by 0 days.

(21) Appl. No.: 10/413,140

(22) Filed: Apr. 15, 2003

(65) Prior Publication Data

US 2003/0205453 A1 Nov. 6, 2003

Related U.S. Application Data

(63) Continuation of application No. 09/757,503, filed on Jan. 11, 2001, now abandoned.

(30) Foreign Application Priority Data

Jan. 12, 2000 (JP) .......................... P2000-006340

(51) Int. Cl.
*C07C 39/12* (2006.01)

(52) U.S. Cl. .................... 568/727; 568/728; 204/157.6

(58) Field of Classification Search ................ 568/727, 568/728; 588/205, 215, 218; 204/157.6
See application file for complete search history.

(56) References Cited

U.S. PATENT DOCUMENTS

| | | | | |
|---|---|---|---|---|
| 3,699,175 | A * | 10/1972 | Coyle | 568/802 |
| 4,216,288 | A * | 8/1980 | Crivello | 430/280.1 |
| 5,004,551 | A | 4/1991 | Sublette | |
| 5,252,722 | A * | 10/1993 | Mandai et al. | 536/4.1 |
| 6,245,822 | B1 * | 6/2001 | Terada et al. | 521/49 |
| 6,483,006 | B1 * | 11/2002 | Sekiguchi et al. | 588/207 |

FOREIGN PATENT DOCUMENTS

| | | | |
|---|---|---|---|
| DE | 42 09 180 | | 9/1993 |
| DE | 195 20 289 | | 2/1997 |
| JP | 61158797 | A * | 7/1986 |
| JP | 05194294 | A * | 8/1993 |
| JP | 09278613 | | 10/1997 |
| JP | 10-84947 | | 4/1998 |
| JP | 10-230243 | | 9/1998 |
| JP | 11-309342 | | 11/1999 |
| WO | WO 200048968 | A1 * | 8/2000 |

OTHER PUBLICATIONS

Holtz, Chem. Abstr. 31:6618 a-c (1931).*
Holtz, Z. physiol. Chem., vol. 248, pp. 5-20 (1937).*
Roberts, "Basic Principles of Organic Chemistry," 1005-1007 (1964).*
Abstract of JP-5-345,189 (1983).
Abstract of JP-11-290,867 (1999).
Office Action of May 28, 2004 relating to JP 09-278613.

* cited by examiner

*Primary Examiner*—Samuel Barts
(74) *Attorney, Agent, or Firm*—Rader, Fishman, & Grauer PLLC; Ronald P. Kananen

(57) ABSTRACT

Ascorbic acid and/or ascorbic acid salt is made to act together with oxygen on an organic compound. Alternatively, light radiation is applied during chemical action with oxygen so as to improve a composition efficiency of an organic compound and obtain a preferable decomposition amount. This reduces the load caused by an organic compound decomposition on the environment.

10 Claims, 1 Drawing Sheet

ORGANIC COMPOUND DECOMPOSING METHOD

The present application is a continuation of the patent application Ser. No. 09/757,503 filed Jan. 11, 2001 now abandoned.

BACKGROUND OF THE INVENTION

1. Field of the Invention

The present invention relates to an organic compound decomposing method having a small load on an environment and with a high decomposition ratio and preferable composition amount.

2. Description of the Related Art

Recently, various substances are pointed out as having a high possibility to become environmental hormones causing a new environment problem such as bisphenol A which is a raw material of plastic, phthalate ester contained in plastic as plasticizer, dioxin generated when waste is burnt, and nonyl phenol which is a surface active agent exhausted from factories and households.

A significant amount of the aforementioned organic compounds is already mixed in the ambient atmosphere, water, and soil. These chemical compounds cannot easily be decomposed in the ecological system. Accordingly, it is expected that these compounds are widely diffused in the entire world through the water circulation and the food chain for a long period of time. This is considered to bring about contamination of the atmosphere, water, and soil, affecting the human body. To cope with this, a technique for purifying the aforementioned organic compounds is strongly required.

For purifying the aforementioned organic compounds, there have been suggested a so-called bio-remediation method for decomposing organic materials by the microbes in the soil and a method for decomposing organic compounds contained in water using supercritical water as disclosed in Japanese Patent Publication 10-84947.

However, the bio-remediation has a problem that the organic compound decomposition speed is slow and it is necessary to continuously supply nutriments for microbes until the organic compound decomposition is complete. There is also a problem that dead bodies of microbes remain after the organic compound decomposition is complete. Moreover, the method for decomposing organic compounds in water using supercritical water requires a large-scale facility and a plenty of energy and cannot be implemented in practice because of the low decomposition capability.

SUMMARY OF THE INVENTION

It is therefore an object of the present invention to provide an organic compound decomposing method having a preferable decomposition efficiency and decomposition amount with a low load on the environment.

The organic compound decomposing method according to the present invention decomposes an organic compound using ascorbic acid and/or ascorbic acid salt together with oxygen.

Ascorbic acid and ascorbic acid salt is well known as vitamin C, available in the natural world, and not harmful. Accordingly, by using these, it is possible to decompose a harmful organic compound without giving a useless load on the environment.

Moreover, the organic compound decomposition is significantly promoted by using the aforementioned substances together with oxygen. That is, this method provides a high decomposition efficiency and can be applied to decomposition of a large amount of organic compound. Moreover, the decomposition operation is quite simple without requiring any large-scale facility, large amount of energy or complicated management.

DETAILED DESCRIPTION OF THE PREFERRED EMBODIMENTS

Figure 1:
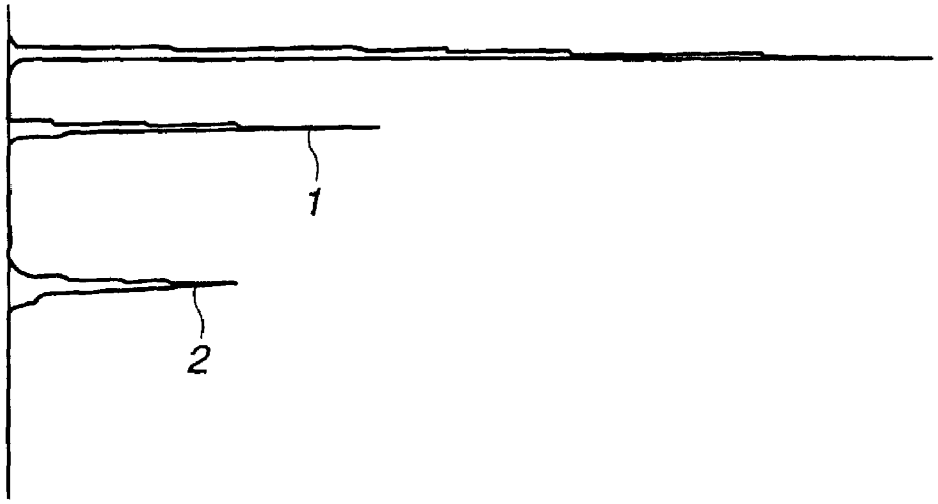
FIG. 1 shows components contained in an aqueous solution of bisphenol A before a treatment using L-sodium ascorbate.

Description will now be directed to embodiments of the present invention. It should be noted that while explanation will be given on decomposition of organic compounds, the present invention is not to be limited to the organic compounds used as examples.

The organic compound decomposing method according to the present invention uses ascorbic acid and/or ascorbic acid salt together with oxygen applied to an organic compound to be treated.

Here, an oxygen gas may be blown directly to the ascorbic acid and/or ascorbic acid salt and the organic compound. However, in order to increase the organic compound decomposition efficiency and decomposition amount, it is preferable to employ a method in which the oxygen is dissolved in a solution together with the ascorbic acid and/or ascorbic acid salt and the organic compound or a method in which oxygen and air are blown into a solution containing ascorbic acid and/or ascorbic acid salt and the organic compound.

Moreover, when considering the handling convenience, it is preferable to add ascorbic acid salt such as sodium salt. The ascorbic acid and the ascorbic acid salt may be extracted from a natural material or synthesized. It should be noted that ascorbic acid extracted from a natural material may contain other components but they will not cause a particular problem.

The amounts of the ascorbic acid and the ascorbic acid salt to be added with respect to an organic compound differ depending on the amount of the organic compound and the decomposition efficiency required. However, it is preferable to be about 1/1000 to 1000 times of the amount of the organic compound and more preferably, about 1/100 to 100 times.

Moreover, the oxygen used here may be an oxygen gas supplied from an oxygen cylinder, or may be the oxygen contained in the air, or may be oxygen contained in a solution. It should be noted that as the oxygen amount is increased, the decomposition efficiency and the decomposition amount of the organic compound are increased. Moreover, when oxygen is dissolved in a solution, for example, as the oxygen concentration is increased such as a saturated concentration, the decomposition efficiency and the decomposition amount of the organic compound are increased.

Moreover, the temperature for the decomposition is preferable from about −20° C. to 120° C. and more preferably, from about 0° C. to 60° C., and most preferably, from about 20° C. to 40° C. When the temperature exceeds 120° C., an enormous energy is required for decomposing the organic compound. Moreover, when the temperature is below −20°

C., the decomposition speed is drastically lowered. It should be noted that pH for the decomposition is preferably from about pH 4 to pH 11.

Here, the organic compounds to be decomposed are not limited to particular compounds, but especially aromatic compounds can be decomposed easily such as nonyl phenol, bisphenol A, dioxin, polychlorinated biphenyl, polybromobiphenyl, alkyl benzene, alkyl benzene derivative, alkylphenol, alkylphenol derivative, phthalate ester, benzophenone, benzophenone derivative, benzoic acid, halogenated benzene derivative, cresol, cresol derivative, aromatic amino acid (such as phenylalanine), agricultural chemicals containing the aromatic ring, resin containing the aromatic ring (such as polystyrene, ABS resin, PET, PC, phenol resin, epoxy resin, polyphenylene oxide, low molecular weight version of polyphenylene oxide, polyphenylene oxide derivative, and the like), dyes containing the aromatic ring, aromatic agent, and the like.

It should be noted that the aforementioned organic compounds can be decomposed with a higher decomposition efficiency and a higher decomposition amount when exposed to the ascorbic acid and/or ascorbic acid salt and oxygen contained in water, i.e., via water, than when exposed directly to the ascorbic acid and/or ascorbic acid salt and oxygen.

Moreover, when the aforementioned organic compounds exist in a gas, it is preferable that the organic compounds in gas be dissolved in an aqueous solution when applied to the ascorbic acid and/or ascorbic acid salt together with oxygen.

As has been described above, by applying the ascorbic acid and/or ascorbic acid salt together with oxygen to the organic compounds, the organic compounds are decomposed. Thus, it is possible to decompose organic compounds harmful to the environment using a method having a high decomposition efficiency and decomposition amount as well as a small load on the environment. Moreover, among the organic compounds, especially those having the aromatic ring can be decomposed.

Moreover, when decomposing the aforementioned organic compounds, it is preferable to add at least one of hydrogen peroxide solution, ozone, ammonium, inorganic alkali, inorganic alkali salt, inorganic acid, inorganic acid salt, porphyrin, and metalloporphyrin.

It should be noted that the amount of the aforementioned substances to be added varies depending on the type and concentration of the organic compound to be decomposed and the temperature during the decomposition. However, the amount to be added is preferably about 1/100 to 100 times with respect to the ascorbic acid and/or ascorbic acid salt and more preferably, from about 1/10 to 10 times.

Thus, by adding the aforementioned substances, the decomposition efficiency and the decomposition amount of an organic compounds are increased.

Moreover, when decomposing an organic compound, it is preferable to apply light. When light is applied, the decomposition efficiency and the decomposition amount of the organic compound are increased.

As has been described above, the organic compound decomposing method according to the present invention enables to decompose harmful organic compounds contained in the domestic waste water, factory waste water, these waste water after disposal, the sea, rivers, soil, exhaust gas, waste, compost, and the like with a high decomposition efficiency and a high decomposition amount as well as with a low energy and a small load on the environment. Moreover, it becomes possible to decompose organic compounds containing the aromatic ring.

Thus, the present invention enables to promote the waste water disposal and changing of waste into compost, purify the soil and the atmosphere, thereby purifying the environment, contributing to the ecology of the earth.

Moreover, since the present invention provides a high decomposition efficiency and a high decomposition amount, it is possible to decompose a large amount of organic compounds. The decomposition operation is quite simple, not requiring a large-scale facility, a large amount of energy, or a complicated management.

Next, explanation will be given on specific examples of the decomposition efficiency and the decomposition amount of organic compounds when the aforementioned organic compound decomposing method is applied.

EXAMPLE 1

Firstly, bisphenol A was added to an aqueous solution of 10 mM sodium hydroxide so as to have a concentration of 2 mM. Next, L-sodium ascorbate was added to this solution so as to have a concentration of 100 mM. Next, this solution was subjected to air bubbling for 4 hours.

Next, compounds contained in the aforementioned solution and compounds contained in the bisphenol A solution not subjected to the aforementioned treatment were detected by using a high performance liquid chromatography (HPLC). Here each of these solutions was added by a benzoic acid solution having a predetermined concentration solved in a mixture of identical amounts of water and ethanol was added as an internal standard liquid.

Figure 2:
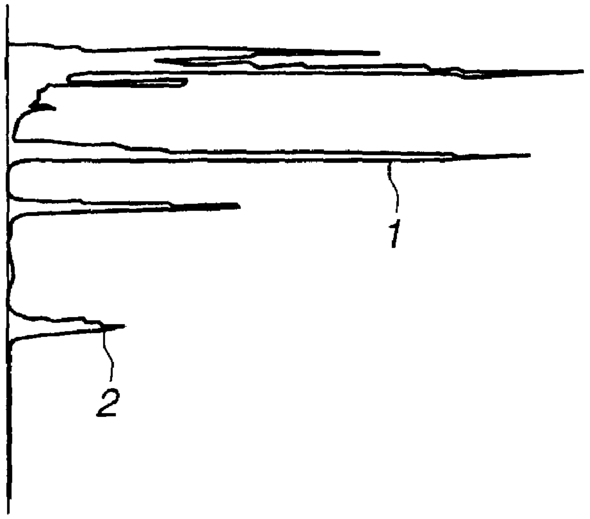
FIG. 2 shows components contained in an aqueous solution of bisphenol A after a treatment using L-sodium ascorbate.

An HPLC analysis of the bisphenol A solution not subjected aforementioned treatment resulted in peak 1 of the benzoic acid and peak 2 of the bisphenol A as shown in FIG. 1. Moreover, an HPLC analysis of the bisphenol A solution subjected to the aforementioned treatment resulted in FIG. 2 where the peak 2 of the bisphenol A is lowered, which means that 75% of the bisphenol A was decomposed.

Moreover, other peaks were observed in addition to peak 1 of the benzoic acid and peak 2 of the bisphenol A. These peaks are considered to be products obtained by decomposition of the bisphenol A.

EXAMPLE 2

Firstly, nonyl phenol ethylene oxide was added to be solved so as to have a concentration of 5 mM. It should be noted that the nonyl phenol ethylene oxide is one of the surface active agents. Next, this solution was added by L-sodium ascorbate with a concentration of 20 mM. Next, this solution was subjected to air bubbling for 6 hours. Here, the water temperature was set to 40° C. As a result, it has been found that 52% of the nonyl phenol ethylene oxide was decomposed.

EXAMPLE 3

Firstly, dodecabromodiphenyl ether is dissolved in a hydrophilic organic solvent, to which a small amount water was added to obtain a concentration of 0.01 mM. Next, to this solution was added L-sodium ascorbate and hydrogen peroxide solution to obtain a concentration of 0.01 mM. Next, this solution was subjected to air bubbling for 12 hours. Here, the water temperature was set to a room temperature. As a result, it has been found that 63% of the dodecabromodiphenyl ether was decomposed.

EXAMPLE 4

Firstly, aqueous solution of diethyl phthalate was dissolved in a hydrophilic organic solvent, to which a small amount of water was added to obtain a concentration of 0.05 mM. Next, to this solution was added L-sodium ascorbate to obtain a concentration of 0.01 mM. Next, this solution was subjected to air bubbling for 6 hours while applying light radiation by a high-pressure mercury lamp to the solution. Here, the water temperature was set to a room temperature. As a result, it has been found that 84% of the aqueous solution of diethyl phthalate was decomposed.

EXAMPLE 5

Firstly, two analytes of strip-shaped polylactic acid were buried in a soil. One of them was kept as it was. The other was subjected to spray of an aqueous solution of L-sodium ascorbate and then the soil containing the sample was subjected to air bubbling for 3 days. As a result, the strip-shaped polylactic acid subjected to the treatment by L-sodium ascorbate was significantly deformed by decomposition.

EXAMPLE 6

After L-sodium ascorbate was added to obtain a concentration of 50 ppm, cation flocculent was added to a contaminated soil subjected to the air season and to a contaminated soil not subjected to the air season. Next, dehydration was performed to each of the soil samples. It should be noted that the contaminated soil is soil in a domestic waste. As a result, it has been found that the dehydration speed of the contaminated soil subjected to treatment by the L-sodium ascorbate was 1.5 times faster than the soil not subjected to the treatment. Moreover, the cake amount after the dehydration was smaller by 2.5%.

EXAMPLE 7

Firstly, L-sodium ascorbate and magnesium porphyrin were added to a colored dye waste water. Here the L-sodium ascorbate was added to obtain a concentration of 20 ppm and the magnesium porphyrin was added to obtain a concentration of 1 ppm. Next, air bubbling was performed for 2 hours. As a result, decoloration of the dye waste water was promoted.

EXAMPLE 8

Firstly, L-sodium ascorbate was added to a semiconductor factory waste water containing 80 ppm of organic carbon (OC) and 30 ppm of hydrogen peroxide solution, so as to obtain a concentration of 5 ppm. Next, air bubbling was performed for 1 hour. As a result, the concentrations of the organic carbon and the hydrogen peroxide solution became equal to or below 10 ppm.

EXAMPLE 9

Firstly, an aqueous solution of L-sodium ascorbate was sprayed to a domestic waste in a treatment machine. Next the waste was agitated sufficiently to mix oxygen in the waste. As a result, the compostization speed was increased by twice as compared in the prior art.

EXAMPLE 10

An organic compound was decomposed by using supercritical water. Here, L-sodium ascorbate having a concentration of 1/10 with respect to the organic compound concentration was added. It should be noted that dissolved oxygen exists in the supercritical water. As a result, the decomposition speed of the organic compound was increased by twice.

EXAMPLE 11

An organic compound was decomposed by using a subcritical water. Here, L-sodium ascorbate having a concentration of 1/10 with respect to the concentration of the organic compound was added. It should be noted that dissolved oxygen exists in the subcritical water. As a result, the decomposition speed of the organic compound was increased by twice.

As is clear from the above-given explanation, the organic compound decomposing method according to the present invention enables to decompose organic compounds contained in domestic waste water, factor waste water, the remaining matters after treatment of these waste waters, in the sea, rivers, soil, exhaust gas, garbage, compost, and the like, with a high decomposition efficiency and a high decomposition amount as well as with a small load on the environment. Thus, it becomes possible to promote waste water treatment and garbage compostization, and purify soils and exhaust gas, thereby promoting purification of the environment, contributing to maintenance of the earth ecology.

Moreover, since the decomposition efficiency and the decomposition amount are preferable, the present invention can also be applied to decomposition of a large amount of organic compounds. Furthermore, the decomposition operation is very simple, not requiring a large-scale facility, large amount of energy, or a complicated management.

What is claimed is:

1. An organic compound decomposing method for decomposing a compound, comprising:

preparing an aqueous solution containing the organic compound to be decomposed as well as at least one of ascorbic acid and ascorbic acid salt; and blowing oxygen into the aqueous solution from at least one of oxygen gas in an oxygen cylinder and oxygen contained in the air wherein the organic compound to be decomposed is at least one selected from a group consisting of nonyl phenol, bisphenol A, dioxin, polychlorinated biphenyl, polybromobiphenyl, alkyl benzene, alkylphenol, phthalate ester, benzophenone, benzoic acid, halogenated benzene, cresol, resin containing the aromatic ring, and dyes containing the aromatic ring.

2. The organic compound decomposing method as claimed in claim 1, wherein at least one selected from a group consisting of hydrogen peroxide solution, ozone, ammonium, inorganic alkali, inorganic alkali salt, inorganic acid, inorganic acid salt, porphyrin, and metalloporphyrin is also used for decomposing the organic compound.

3. The organic compound decomposing method as claimed in claim 1, wherein the decomposition is performed while applying light radiation.

4. The organic compound decomposing method as claimed in claim 3, where the light radiation is applied using a high-pressure mercury lamp.

5. The organic compound decomposing method as claimed in claim 1, wherein the amount of ascorbic acid and ascorbic acid salt added to the aqueous solution is from about 1/1000 to about 1000 times the amount of organic compound added to the aqueous solution.

6. The organic compound decomposing method as claimed in claim 1, wherein the amount of ascorbic acid and ascorbic acid salt added to the aqueous solution is from about 1/100 to about 100 times the amount of organic compound added to the aqueous solution.

7. The organic compound decomposing method as claimed in claim 1, wherein the temperature for the decomposition is from about −20° C. to about 120° C.

8. The organic compound decomposing method as claimed in claim 1, wherein the temperature for the decomposition is from about 0° C. to about 60° C.

9. The organic compound decomposing method as claimed in claim 1, wherein the temperature for the decomposition is from about 20° C. to about 40° C.

10. The organic compound decomposing method as claimed in claim 1, wherein the pH for the decomposition is from about pH 4 to about pH 11.

* * * * *